US00PP22967P3

(12) United States Plant Patent
Egger

(10) Patent No.: US PP22,967 P3
(45) Date of Patent: Aug. 14, 2012

(54) ***HEUCHERA* PLANT NAMED 'CHERRY COLA'**

(50) Latin Name: ***Heuchera* sp.**
Varietal Denomination: Cherry Cola

(75) Inventor: Janet Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 67 days.

(21) Appl. No.: 12/930,854

(22) Filed: Jan. 19, 2011

(65) Prior Publication Data

US 2012/0185986 P1 Jul. 19, 2012

(51) Int. Cl.
*A01H 5/00* (2006.01)

(52) U.S. Cl. ..... Plt./440

(58) Field of Classification Search ..... Plt./440
See application file for complete search history.

*Primary Examiner* — Jane Hwu
(74) *Attorney, Agent, or Firm* — Jondle & Associates, P.C.

(57) ABSTRACT

A new and distinct *Heuchera* plant characterized by medium red brown leaves year round, very free flowering on medium to short flower stalks, soft red flowers on red peduncles, well branched, mounding habit, and excellent vigor.

1 Drawing Sheet

Botanical denomination: *Heuchera* sp.

Variety designation: 'Cherry Cola'.

Cross Reference to: *Heuchera* 'Root Beer' applied for concurrently (U.S. Plant patent application Ser. No. 12/932,453).

BACKGROUND OF THE INVENTION

The present invention relates to a new and distinct cultivar of *Heuchera* and given the cultivar name of 'Cherry Cola'. *Heuchera* is in the family Saxifragaceae. *Heuchera* 'Cherry Cola' originated from a cross between *Heuchera* 747-5, a proprietary non-commercial hybrid, as the seed parent, and *Heuchera* 766-5, a proprietary non-commercial hybrid, as the pollen parent.

Compared to the seed parent, *Heuchera* 747-5, the new cultivar has smaller leaf size and red brown rather than rose to olive leaf color.

Compared to the pollen parent, *Heuchera* 766-5, the new cultivar has red rather than light pink to white flowers and red brown rather than purple black leaves.

Compared to its sibling *Heuchera* 'Root Beer', the new cultivar has lighter colored leaves and red rather than creamy yellow flowers.

This new *Heuchera* is uniquely distinguished by:

1. medium red brown leaves year round,
2. very free flowering on medium to short flower stalks,
3. soft red flowers on red peduncles,
4. well branched, mounding habit, and
5. excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

The photo shows a 2-year-old plant of *Heuchera* 'Cherry Cola' growing in the ground in full sun in the garden in May in Canby, Oreg.

DETAILED PLANT DESCRIPTION

The following is a detailed description of the new *Heuchera* cultivar based on observations taken in April of 2-year-old specimens growing in the ground in the garden in full sun in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form.*—Basal rosette, herbaceous perennial.
*Hardiness.*—USDA Zone 4 to 9.
*Size.*—23 cm tall from top of the foliage to the ground and 41 cm wide.
*Habit.*—Mounding.
*Vigor.*—Excellent.

Leaf:

*Type.*—Simple.
*Arrangement.*—Rosette.
*Shape.*—Broadly ovate to orbicular.
*Lobing/division.*—5 to 7 shallow lobes, shallow secondary lobes.
*Venation.*—Palmate.
*Margins.*—Broadly crenate.
*Apex.*—Mucronulate.
*Base.*—Cordate, lobes usually overlapping at the base.
*Blade size.*—Grows to 8.5 cm long and 9.3 cm wide.
*Texture.*—Leathery.

*Surface texture*.—Pubescent on top side, glandular on bottom.

*Petiole description*.—Grows to 16 cm long and 2.5 mm wide, glandular hairs, closest to Purple 77B.

*Leaf color*.—Topside, spring to summer leaves are between Greyed Red 181A and Greyed Orange 176A, bottom side Greyed Purple 184A; winter leaves topside are Brown 200B with areas of Greyed Purple 185C, bottom side Purple N77A.

Inflorescence:

*Size*.—Grows to 3.5 cm wide and 18 cm long.

*Type*.—Thyrse.

*Number of flowers per thyrse*.—About 90.

*Number of thyrse*.—About 55 in the first spring flush.

*Peduncle*.—Grows to 27 cm long, 4 mm wide at base, Greyed Purple 187B, glandular hairs, usually with 0 to 2 small pedicellate cauline leaves (grow to 17 mm long and 17 mm wide, ovate to orbicular, 3 lobed, margins sharply crenate to serrate, tip mucronulate, base cordate).

*Pedicel*.—Variable in size, with glandular hairs, Greyed Purple 187B.

*Bloom period*.—April through June in Canby, Oreg.

Flower bud:

*Size*.—2.5 mm wide and 3 mm long.

*Description*.—Glandular puberulent, ovoid, down facing.

*Color*.—Red 47A.

Flower:

*Type*.—Perfect.

*Shape*.—Campanulate.

*Size*.—6 mm long and 6 mm wide.

*Corolla description*.—5 petals, 3 mm long and 1.2 mm wide, spatulate with one to two side lobes, margins entire, tip acute, glabrous on top, glandular on bottom side, top and bottom sides Red Purple 68A.

*Calyx description*.—Campanulate, 5 mm long and 6 mm wide, with 5 lobes divided ½ way to the base, each 2 mm wide and 3 mm long, glandular hairs outside and inside, tips obtuse, margin entire; color both sides Orange Red N34C with tips Red 53A.

*Stamen description*.—5 in number, filaments 3 mm long, White 155D, anthers 0.4 mm, Orange Red 31B, pollen Yellow Orange 21A.

*Pistil description*.—1, 2-beaked, 4.5 mm long and 2 mm wide; Green Yellow 1D overall, ovary 2 mm long and 2 mm wide; style 2.5 mm long.

*Fragrance*.—None.

*Lastingness*.—Each thyrse blooms for about 3 weeks on the plant.

Fruit:

*Type*.—Two-beaked ovoid capsule.

*Fertility*.—Low.

*Color*.—Greyed Brown 199C.

Seed:

*Shape*.—Linear.

*Size*.—2 mm long.

*Color*.—Black 202A.

Pest and disease tolerance: Excellent disease resistance to powdery mildew, the common problem of *Heuchera*. Susceptible to *Heuchera* rust and root weevils.

I claim:

1. A new and distinct *Heuchera* plant as herein illustrated and described.

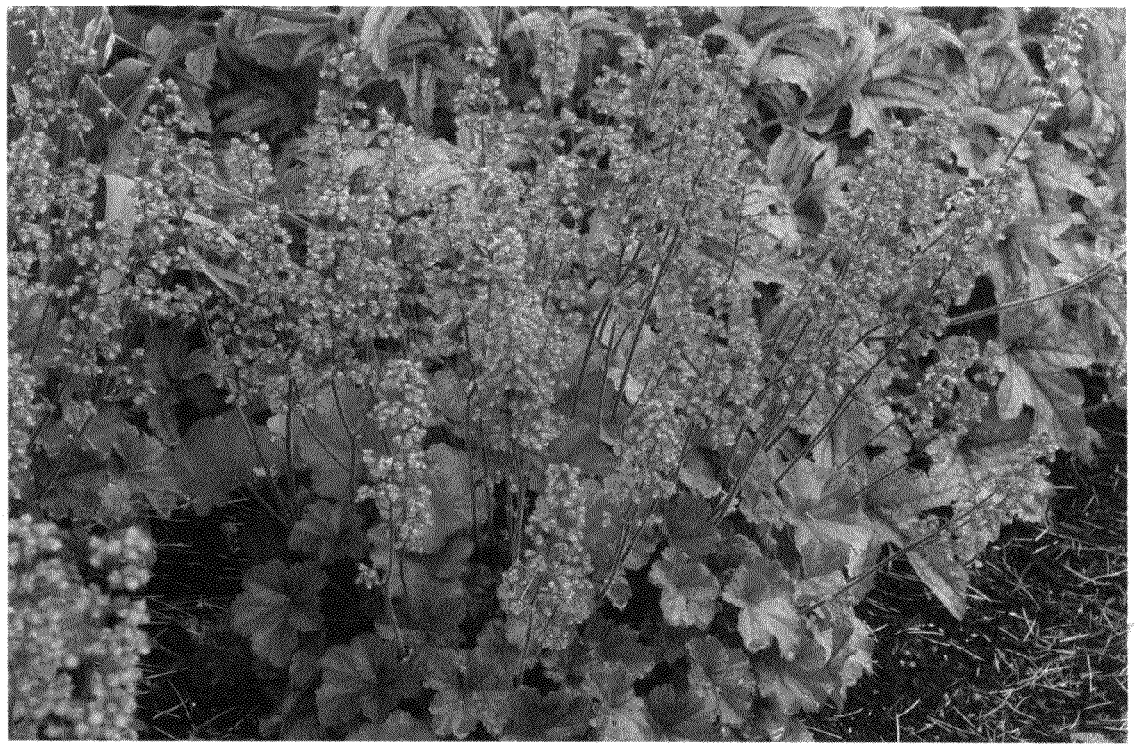

* * * * *